US010086045B2

(12) United States Patent
Cameron (10) Patent No.: US 10,086,045 B2
(45) Date of Patent: Oct. 2, 2018

(54) METHODS OF TREATMENT USING STEM CELL MOBILIZERS

(71) Applicant: THE JOHNS HOPKINS UNIVERSITY, Baltimore, MD (US)

(72) Inventor: Andrew MacGregor Cameron, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/254,526

(22) Filed: Sep. 1, 2016

(65) Prior Publication Data

US 2017/0340709 A1   Nov. 30, 2017

Related U.S. Application Data

(63) Continuation of application No. 13/636,733, filed as application No. PCT/US2011/029634 on Mar. 23, 2011.

(60) Provisional application No. 61/316,481, filed on Mar. 23, 2010.

(51) Int. Cl.
| | | |
|---|---|---|
| *A61K 38/21* | (2006.01) | |
| *A61K 38/19* | (2006.01) | |
| *A61K 31/4427* | (2006.01) | |
| *A61K 31/395* | (2006.01) | |

(52) U.S. Cl.
CPC .......... *A61K 38/193* (2013.01); *A61K 31/395* (2013.01); *A61K 31/4427* (2013.01)

(58) Field of Classification Search
CPC ............................ A61K 38/193; A61K 31/395
See application file for complete search history.

(56) References Cited

U.S. PATENT DOCUMENTS

| | | |
|---|---|---|
| 6,825,351 B2 | 11/2004 | McEachern et al. |
| 6,835,731 B2 | 12/2004 | Bridger et al. |
| 2004/0191215 A1 | 9/2004 | Froix et al. |
| 2006/0281754 A1* | 12/2006 | Oben .................. A61K 31/517 514/252.17 |
| 2008/0038269 A1* | 2/2008 | Susan ................ A01K 67/0275 424/139.1 |
| 2008/0274109 A1 | 11/2008 | Gentz et al. |
| 2010/0178271 A1 | 7/2010 | Bridger et al. |
| 2011/0135651 A1* | 6/2011 | Geiger ............... A61K 38/1808 424/145.1 |

FOREIGN PATENT DOCUMENTS

| | | |
|---|---|---|
| WO | 200067776 A1 | 11/2000 |
| WO | 2008019371 A1 | 2/2008 |
| WO | 2009067245 A2 | 5/2009 |

OTHER PUBLICATIONS

Stravitz et al., (2009) Management of acute liver failure., Nat Rev. Gastroenterol. Hepatol. 6, 542-53.
Lee et al., (2008) Acute Liver Failure: summary of a workshop., Hepatology 47, 1401-15.
Farmer et al., (2003) Liver transplantation for fulminant hepatic failure: experience with more than 200 patients over a 17-year period., ANN. Surg 237(5), 666-75.
Liu et al., (2009) Transplanted Endothelial Progenitor Cells Ameliorate Carbon Tetrachloride-induced Liver Cirrhosis in Rats., Liver Transplantation 1092-1100.
Uy et al., (2008), Plerixafor, a CXCR4 antagonist for the mobilization of hematopoietic., Expert Opinion on Biologic Therapy, 8(1) 1797-1804.
Sun et al., (2009) Recruitment of host progenitor cells in rat liver transplants, Hepatology 49(2), 587-97.
Bilan et al., (2002) Structure of a fucoidan from the brown seaweed *Fucus evanescens* C.Ag., Carbohydrate Research 337(8) 719-30.
Pomin et al., (2005) Mild acid hydrolysis of sulfated fucans: a selective 2-desulfation reaction and an alternative approach for preparing tailored sulfated oligosaccharides, Glycobiology 15(12) 1376-85.
Melo et al., (2004) Antithrombin-mediated Anticoagulant Activity of Sulfated Polysaccharides., J Biol Chem 279(2), 20835.
Farias et al., (2000) Structure and anticoagulant activity of sulfated galactans. Isolation of a unique sulfated galactan from the red algae *Botryocladia occidentalis* and comparison of its anticoagulant action with that of sulfated galactans from invertebrates., J. Biol. Chem, 275(38) 29299-29307.
Gaia et al., (2006), Feasability and safety of G-CSF administration to induce bone marrow-derived cells mobilization in patients with end stage liver disease., Journal of Hepatology 45, 13-19.
Lorenzini et al., (2008) Stem cell mobilization and collection in patients with liver cirrhosis., Ailment Pharmacol Ther 27, 932-39.
Di Campli et al., (2007) Safety and efficacy profile of G-CSF therapy in patients with acute on chronic liver failure., Digestive and Liver Disease 39, 1071-1076.
Okumoto et al., (2007), Serum Levels of stem cell factor and thrombopoietin are markedly decreased in fulminant hepatic failure patients with a poor prognosis., 39, 1071-76.
Eroglu et al., (2002), Effect of granulocyte-macrophage colony-stimulating factor on hepatic regeneration after 70% hepatectomy in normal and cirrhotic rats., HPB 4(2): 67-73.
Nienaber et al., (2006) Effects of granulocyte-colony-stimulating factor on mobilization of bone-marrow-derived stem cells after myocardial infarction in humans., Nature Clinical Practice Cardiovascular Medicine 3, S73-77.
Miyazaki et al., (2007) Isolation of a Bone Marrow-Derived Stem Cell Line with High Proliferation Potential and its Application for Preventing Acute Fatal Liver Failure., Stem Cells., 25:2855-2863.
Kuo et al., (2008) Stem Cell Therapy for liver disease: parameters governing the success of using bone marrow mesenchymal stem cells., Gastroenterology., 134:2111-121.

(Continued)

*Primary Examiner* — Gyan Chandra
(74) *Attorney, Agent, or Firm* — Johns Hopkins Technology Ventures (57) ABSTRACT

The present invention relates to the field of stem cells. In one aspect, the present invention provides methods of treating a subject with acute liver injury comprising administering to the subject a therapeutically effective amount of at least one stem cell mobilizer. In particular embodiments, the subject is treated with plerixafor and granulocyte colony-stimulating factor (G-CSF).

12 Claims, 6 Drawing Sheets

(56) References Cited

OTHER PUBLICATIONS

Ince et al., (2005) Prevention of left ventricular remodeling with granulocyte colony-stimulating factor after acute myocardial infarction., Circulation, 112:173-180.

Leone et al., (2006) Endogenous G-CSF and CD34 cell mobilization after acute myocardial infarction., International Journal of Cardiology, 111: 202-208.

De Silvestro et al., (2004) Mobilization of peripheral blood hematopoietic stem cells following liver resection surgery., Hepatogastroenterology, 51(57): 805-810.

Di Campli et al., (2005) No evidence of hematopoietic stem cell mobilization in patients submitted to hepatectomy or in patients with acute on chronic liver failure., Transplantation Proceedings, 37:2563-66.

Stokman, G., et al., (2005) ", Hematopoietic Stem Cell Mobilization Therapy Accelerates Recovery of Renal Function Independent of Stem Cell Contribution" J Am Soc Nephrol 16: 1684-1692.

\* cited by examiner

Figure 5. Mobilization of CD34+ Bone Marrow Stem Cells in Pigs

Figure 6. Successful Liver Transplantation in Swine

FIG. 6A-6I

METHODS OF TREATMENT USING STEM CELL MOBILIZERS

CROSS-REFERENCE TO RELATED APPLICATIONS

This application is a Continuation of U.S. patent application Ser. No. 13/636,733, filed Feb. 26, 2014, which is a 35 U.S.C. § 371 U.S. national entry of International Application PCT/US2011/029634 having an international filing date of Mar. 23, 2011, which claims the benefit of U.S. Provisional Application No. 61/316,481, filed Mar. 23, 2010, the content of each of the aforementioned applications is herein incorporated by reference in their entirety.

FIELD OF THE INVENTION

The present invention relates to the field of stem cells. More particularly, the methods and compositions of the present invention are useful for mobilizing stem cells to treat a variety of conditions including acute liver injury, and more particularly, acute liver failure (ALF).

BACKGROUND OF THE INVENTION

Acute liver failure (ALF) affects over two thousand Americans per year and results in approximately four hundred liver transplants annually. Defined as the abrupt loss of hepatocellular function in patients with previously normal liver function, the most common etiologies are acetaminophen overexposure and acute viral hepatitis. See Stravitz et al., 6 NAT REV. GASTROENTEROL. HEPATOL. 542-53 (2009). In the most severe cases, patients manifest a rapidly developing coagulopathy, and encephalopathy that progresses to cerebral herniation and death without prompt liver transplantation. See Lee et al., 47 HEPATOLOGY 1401-15 (2008). Fewer than half of patients with ALF will spontaneously recover with supportive care alone, yet at present, no pharmacologic or adjunct therapies have been shown to be of benefit in this clinical scenario. For these critically ill patients, liver transplantation frequently represents the only option for survival; however, this limited resource may be inaccessible at the time at which it is emergently needed. Furthermore, the decision to proceed to transplantation is not always straightforward, because some patients will spontaneously recover, but the ability to predict recovery is markedly limited. Under aggressive utilization of liver transplantation can result in devastating outcomes in potentially salvageable patients, while overly aggressive utilization of transplantation both commits patients who might have spontaneously recovered to a lifetime of immunosuppression, and also unnecessarily utilizes precious grafts that could be allocated to others in need. New therapies, particularly those that can promote spontaneous recovery and lessen the need for liver transplantation, are badly needed.

SUMMARY OF THE INVENTION

The present invention is based, in part, on the discovery that the administration of at least one stem cell mobilizer can be used to treat subjects with acute liver injury. As described herein, the present inventors use pharmacologic mobilization of endogenous HSCs in the setting of liver injury to show that these cells can be of therapeutic benefit. The present invention shows survival advantage from the treatment provided, specifically, an elevation of serum leukocytes and CD34+ cells in animals treated with plerixafor and G-CSF. The present invention demonstrates the rapid appearance of CD34+ cells in the livers of only the animals who undergo injury and stem cell mobilization. These cells could differentiate into hepatocytes to directly support an animal with inadequate liver mass or perhaps supply some sort of paracrine support to mitigate injury or accelerate ongoing local repair mechanisms.

Accordingly, in one aspect, the present invention provides methods and compositions useful for treating subjects with acute livery injury. In a specific embodiment, a method for treating a subject with acute liver injury comprises administering to the subject a therapeutically effective amount of at least one stem cell mobilizer. The acute liver injury can include, but is not limited to, acute liver failure and post-surgical resection.

The at least one stem cell mobilizer can be any stem cell mobilizer, and without limitation, can be selected from the group consisting of plerixafor, AMD3465, NIBR1816, TG-0054, G-CSF, GM-CSF, SDF-1, and SCF. In particular embodiments, the subject is treated with plerixafor and G-CSF.

In specific embodiments, the present invention provides methods for treating a subject with acute liver failure comprising administering to the subject a therapeutically effective amount of at least one stem cell mobilizer. In a more specific embodiment, the method for treating a subject with acute liver failure comprises administering to the subject a therapeutically effective amount of plerixafor and a therapeutically effective amount of G-CSF.

In further embodiments, the present invention provides methods for treating an organ transplant recipient comprising administering to the recipient a therapeutically effective amount of at least one stem cell mobilizer. The treatment regimen can be applied to any type of organ transplant including liver, kidney, skin, heart, lung, intestine, and pancreas. The treatment regimen can also be applied to composite tissue transplantation. The composite tissue can be hand, face, or any other anatomical part. In general, however, the present invention is useful in the treatment of patients with ischemic injury and/or shock.

More specifically, in one embodiment, a method of treating an organ transplant recipient comprises administering to the recipient a therapeutically effective amount of at least one stem cell mobilizer. The transplanted organ can be selected from the group consisting of liver, kidney, skin, heart, lung, intestine, and pancreas. In a specific embodiment, the organ is liver.

In an even more specific embodiment, a method of treating a liver transplant recipient comprises administering to the recipient a therapeutically effective amount of at least one stem cell mobilizer. In another embodiment, a method of treating a kidney transplant recipient comprising administering to the recipient a therapeutically effective amount of at least one stem cell mobilizer. In yet another embodiment, a method of treating a skin transplant recipient comprises administering to the recipient a therapeutically effective amount of at least one stem cell mobilizer. In a further embodiment, a method of treating a patient diagnosed with ischemic injury comprises administering to the patient a therapeutically effective amount of at least one stem cell mobilizer. In another specific embodiment, a method of treating a composite tissue transplant recipient comprises administering to the recipient a therapeutically effective amount of at least one stem cell mobilizer. In yet a further embodiment, at least one stem cell mobilizer may be used to treat subjects with acute pancreatitis, myocardial infarction, and/or generally conditions involving parenchymal insufficiency.

In the foregoing embodiments, the stem cell mobilizer can be any stem cell mobilizer including, but not limited to, plerixafor, AMD3465, NIBR1816, TG-0054, G-CSF, GM-CSF, SDF-1, and SCF. In a specific embodiment, the stem cell mobilizer is a CXCR4 antagonist. In a more specific embodiment, the stem cell mobilizer is plerixafor. In another embodiment, the stem cell mobilizer is NIBR1816. In particular embodiments, the transplant recipient is treated with plerixafor and G-CSF. In another embodiment, the transplant recipient is treated with NIBR1816 and G-CSF. In a further embodiment, the transplant recipient is treated with TG-0054 and G-CSF.

Thus, in one aspect, a first stem cell mobilizer is administered in combination with a second stem cell mobilizer. In particular embodiments, the first stem cell mobilizer (e.g., plerixafor) and second stem cell mobilizer (e.g., G-CSF) is administered separately or co-administered over a period of time following injury (e.g., ALF). For example, the treatment regimen for a patient suffering from ALF may comprise the following: plerixafor (2 mg/kg) and G-CSF (300 µg/kg) at Day 0, 1, 2, and 3 (subcutaneous injection). In other embodiments, the dosage regimen for a patient may comprise NIBR1816 (30 mg/kg) and G-CSF (300 µg/kg).

Alternatively, plerixafor can be administered in a dose of about 10 µg to about 10 mg per kg of body weight, about 100 µg to about 5 mg per kg of body weight, about 200 µg to about 3 mg per kg of body weight, about 300 µg to about 2 mg per kg of body weight, or any range or value of the foregoing. In one embodiment, the dose of plerixafor can be about 1 mg to about 4 mg/kg. In a specific embodiment, plerixafor can be administered at a dose of about 2 mg/kg of body weight.

Other CXCR4 antagonists like NIBR1816 can be administered in a dose of about 1 mg to about 60 mg per kg of body weight, about 10 mg to about 50 mg per kg of body weight, about 20 mg to about 40 mg per kg of body weight, about 25 µg to about 45 mg per kg of body weight, or any range or value of the foregoing. In one embodiment, the dose of NIBR1816 can be about 25 mg to about 35 mg/kg. In a specific embodiment, NIBR1816 can be administered at a dose of about 30 mg/kg of body weight.

A CXCR4 antagonist like TG-0054 can be administered in a dose of about 0.1 mg to about 10 mg per kg of body weight, about 0.5 mg to about 8 mg per kg of body weight, about 1 mg to about 6 mg per kg of body weight, about 1.5 mg to about 5 mg per kg of body weight, or any range or value of the foregoing. In one embodiment, the dose of TG-0054 can be about 2 mg to about 5 mg/kg. In a specific embodiment, TG-0054 can be administered at a dose of about 4 mg/kg of body weight.

Such doses can be administered within about 1 hour to about 96 hours following injury (e.g., acute liver injury, acute liver failure, ischemic injury, etc.), within about 1 hour to about 72 hours, within about 1 to about 48 hours, within about 1 to about 24 hours, and within about 2 hours to about 12 hours following injury. In the cases of transplant, a stem cell mobilizer (e.g., a CXCR4 antagonist) can be administered several days to several hours prior to surgery.

G-CSF can be administered in a dose of about 1 µg to about 3 mg per kg of body weight, about 5 µg to about 2 mg per kg, about 10 µg to about 1 mg per kg, about 50 µg to about 900 µg per kg, and about 100 µg to about 500 µg per kg, or any range or value of the foregoing. In certain embodiments, the dose of G-CSF can be about 200 µg to about 400 µg per kg. In a specific embodiment, G-CSF can be administered at a dose of about 300 µg/kg of body weight.

Such doses can be administered within about 1 hour to about 96 hours following injury (e.g., acute liver injury, acute liver failure, ischemic injury, etc.), within about 1 hour to about 72 hours, within about 1 to about 48 hours, within about 1 to about 24 hours, and within about 2 hours to about 12 hours following injury. In the cases of transplant, G-CSF can be administered several days to several hours prior to surgery.

BRIEF DESCRIPTION OF THE FIGURES

FIG. 1A-1C describes mortality and hepatic injury after injection of carbon tetrachloride ($CCl_4$). FIG. 1B is a graph displaying peak liver function test (LF) results, specifically, serum aspartate transaminase (AST) (dark bars) and alanine transaminase (ALT) (light bars) levels in mice (n=2) 24 hrs and 96 hrs after intraperitoneal injection of $CCL_4$ at 4 ml/kg compared to baseline levels in uninjected animals (0 hrs).

FIG. 2A-2C displays hematopoietic stem cell mobilization response in to plerixafor and/or G-CSF administration. Rats (n=3 per treatment group) were administered a single dose of plerixafor (2 mg/kg), G-CSF (300 µg/kg) or both. FIG. 2B is a graph showing increases in $CD34^+$ cells in rodent in response to plerixafor and/or G-CSF.

FIG. 3A-3B demonstrates that plerixafor and G-CSF administration improves survival and lessens hepatic injury after injection of $CCl_4$.

FIG. 4A-4B shows CD34 immunostaining of rat livers 24 hours after stem cell mobilization. Representative images from control uninjured animals administered neither $CCl_4$ nor plerixafor/G-CSF (FIG. 4A, panel 1), $CCl_4$ injected animals administered saline control (FIG. 4A, panel 2), uninjured animals administered plerixafor/G-CSF (FIG. 4A, panel 3), and $CCl_4$ injected animals administered plerixafor/G-CSF (FIG. 4A, panel 4).

FIG. 5 shows that the absolute number of CD34+ cells in per ml blood was significantly increased in a time-dependent fashion, and reached peak levels at 3 hours after subcutaneous injection of plerixafor.

FIG. 6A-6I shows that successful establishment of a pig liver transplant model. Utilizing 20 kg miniature swine (FIG. 6A) in a large animal operating room (FIG. 6B), orthotopic liver transplantations were successfully performed in under 3 hours for both donor and recipient procedures (n=5). Utilizing a midline laparotomy in the recipient (FIG. 6C), a hepatectomy was performed after the donor organ had been procured. Transplantation consisted of a suprahepatic (FIG. 6D) and infrahepatic (FIG. 6E) vena caval anastomosis followed by reconnection of the portal vein (FIG. 6F) and graft reperfusion. The hepatic artery was sewn after an aortic conduit had been constructed utilizing donor iliac artery (FIG. 6G), and finally the bile duct anastomosis was constructed in an end-to-end fashion (FIG. 6H). The liver had a normal appearance at the end of the procedure (FIG. 6I) and the animals tolerated the relatively short operation well.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Patients with ALF represent a challenging group. Untreated, they have high mortality rates, though if they survive they will return to normal functioning spontaneously. There is a life-saving therapy available, but it is a resource badly needed by others who have no hope of spontaneous recovery and survival rates after transplant for ALF are known to be far inferior to that of liver transplant for other indications. See Farmer et al., 237(5) ANN. SURG. 666-75 (2003). ALF patients are often critically ill, and decisions must be made rapidly. Novel medical therapies that improve the rate of spontaneous recovery in these patients would be extraordinarily helpful.

Why the liver fails to use all possible recovery pathways, e.g., recruitment of endogenous marrow-derived stem cells, in these scenarios of massive insult is unclear. Augmenting the release of marrow-bound stem cells has been well studied and optimized for utilization in a very different group of patients who donate via pheresis for subsequent hematopoietic stem cell (HSC) autotransplantation after chemoablation of their lymphoma or myeloma. Meanwhile, efforts to augment liver recovery from injury with stem cells have thus far focused on provision of exogenous stem cells with success demonstrable in some animal models. See Liu et al., 15 LIVER TRANSPLANTATION 1092-1100 (2009).

Plerixafor was initially studied as an anti-human immunodeficiency virus (HIV) drug as it was found to be a small molecule antagonist of CXCR4, then known as an HIV coreceptor. See Uy et al., 8(1)) EXPERT OPINION ON BIOLOGIC THERAPY 1797-1804 (20080. CXCR4 also binds stromal-derived factor 1 (SDF-1) and this interaction anchors HSCs to their niche in the bone marrow. Elevated levels of SDF elsewhere in the body, i.e., at the site of injured tissue, create a gradient that releases stem cells from the marrow, perhaps so that they may participate in tissue repair elsewhere in the body. Why this process is not more efficient in settings like massive liver injury is unclear. Plerixafor was not an effective anti-HIV agent in vivo but resulted in massive mobilization of HSCs to the periphery when given to healthy volunteers.

I. Definitions

The term "acute liver injury" refers to liver injury of rapid onset leading to abnormal liver enzyme and/or protein levels. Standard liver function tests can be used to assay liver enzymes including, but not limited to, alanine transaminase (ALT), aspartate transaminase (AST), alkaline phosphatase, and gamma glutamyl transpeptidase (GGT), as well as protein levels including, but not limited to, albumin (ALB), total bilirubin (TBIL), and direct or conjugated bilirubin. Other tests commonly requested alongside liver function tests that may be used to determine liver injury include 5' nucleotidase (5'NTD), coagulation test (e.g., international normalized ration (INR)), serum glucose (Glu), and lactate dehydrogenase (LDH)

"Acute Liver Failure" or "ALF" is encompassed within the term acute liver injury. ALF "ALF" generally refers to the abrupt loss of hepatocellular function in patients with previously normal liver function. The rapid deterioration of liver function results in coagulopathy and alteration in the mental status of a previously healthy individual. ALF often affects young people and carries a very high mortality. In certain embodiments, the term ALF can be used to describe the development of coagulopathy, generally an international normalized ratio (INR) of greater than about 1.5, and optionally any degree of mental alteration (encephalopathy) in a patient without preexisting cirrhosis and with an illness of less than about 26 weeks duration.

ALF encompasses both fulminant hepatic failure (FHF) and subfulminant hepatic failure (or late-onset hepatic failure). FHF is generally used to describe the development of encephalopathy within 8 weeks of the onset of symptoms in a patient with a previously healthy liver. Subfulminant hepatic failure is reserved for patients with liver disease for up to 26 weeks before the development of hepatic encephalopathy.

Current clinical management paradigms for acute liver failure (ALF) are largely supportive. Severe liver injury associated with rapid loss of liver function is often lethal, and patients require liver transplantation or die. Even with optimal early management, many patients develop a cascade of complications often associated with a systemic inflammatory response syndrome, resulting in multisystem organ failure.

In the United States and western countries, drug-induced liver injury is the predominant etiology of ALF, with suicidal intent the reason for nearly half of the cases. However, idiosyncratic drug reactions are increasingly common. Worldwide, viral hepatitis is the leading cause of ALF.

Although the following description describes embodiments in the context of subjects with acute liver injury, including ALF, it is understood that the following description encompasses the application of the present invention in other settings as well. In certain embodiments, quick recovery after surgical resection or larger surgical resections could be facilitated using the methods of the present invention. In other embodiments, the methods and compositions of the present invention can be used to treat organ and composite tissue transplant recipients. Transplant applications might include the ability to use ever more extended criteria grafts, or ever small living donor grafts, which would then serve as scaffolds for endogenous repopulation by mobilized host stem cells. Such a pharmacologically driven graft repopulation by recipient cells may lead to an eventual conversion of the donor graft to recipient phenotype creating a novel type of tolerance protocol. See Sun et al., 49(2) HEPATOLOGY 587-97 (2009). Applications with other tissues in other injury scenarios are possible as well, including use of the present invention in subjects following myocardial infarction, acute kidney injury, and/or acute pancreatitis, generally scenarios that involve parenchymal insufficiency.

"Agent" refers to any and all materials that may be used as or in pharmaceutical compositions, including any and all materials such as small synthetic or naturally derived organic compounds, nucleic acids, polypeptides, antibodies, fragments, isoforms, variants, or other materials that may be used independently for such purposes, all in accordance with the present invention.

"Antagonist" refers to an agent that down-regulates (e.g., suppresses or inhibits) at least one bioactivity of a protein. An antagonist may be an agent which inhibits or decreases the interaction between a protein and another molecule, e.g., a target peptide or enzyme substrate. An antagonist may also be an agent that down-regulates expression of a gene or which reduces the amount of expressed protein present.

"Hematopoiesis" refers to the highly orchestrated process of blood cell development and homeostasis. Prenatally, hematopoiesis occurs in the yolk sack, then liver, and eventually the bone marrow. In normal adults it occurs in bone marrow and lymphatic tissues.

The terms "stem cells" and "hematopoietic stem cells" are used interchangeably herein. Stem cells are distinguished from other cell types by two important characteristics. First, stem cells are unspecialized cells capable of renewing themselves through cell division, sometimes after long periods of inactivity. Second, under certain physiologic or experimental conditions, stem cells can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions.

The term "stem cells" can refer to multipotent stem cells that are capable of differentiating into all blood cells including erythrocytes, leukocytes and platelets. For instance, the "hematopoietic stem cells" or "stem cells" as used in the present invention are contained not only in bone marrow but also in umbilical cord blood derived cells.

A "stem cell mobilizer," "mobilizer of hematopoietic stem cells or progenitor cells" or "mobilize," (used interchangeably), as described herein, refers to any agent, whether it is a small organic molecule, synthetic or naturally derived, or a polypeptide, such as a growth factor or colony stimulating factor or an active fragment or mimic thereof, a nucleic acid, a carbohydrate, an antibody, or any other agent that acts to enhance the migration of stem cells from the bone marrow into the peripheral blood. A stem cell mobilizer may increase the number of hematopoietic stem cells or hematopoietic progenitor/precursor cells in the peripheral blood, thus allowing for a more accessible source of stem cells. In particular embodiments, a stem cell mobilizer refers to any agent that mobilizes CD34+ stem cells. It is further understood that an agent may have stem cell mobilizing activity in addition to one or more other biological activities including, but not limited to, immunosuppression. An example of such an agent is Tacrolimus (also FK-506 or Fujimycin). Tacrolimus is sold under the trade names Prograf® (given twice daily), Advagraf® (a sustained release formulation allowing once daily dosing), and Protopic® (a topical formulation).

A "patient," "subject," or "host" to be treated by the present methods refers to either a human or non-human animal, such as primates, mammals, and vertebrates. In particular, the terms refer to a human.

A "small molecule" refers to a composition that has a molecular weight of less than 3 about kilodaltons (kDa), less than about 1.5 kilodaltons, or less than about 1 kilodalton. Small molecules may be nucleic acids, peptides, polypeptides, peptidomimetics, carbohydrates, lipids or other organic (carbon-containing) or inorganic molecules. A "small organic molecule" is an organic compound (or organic compound complexed with an inorganic compound (e.g., metal)) that has a molecular weight of less than about 3 kilodaltons, less than about 1.5 kilodaltons, or less than about 1 kDa.

As used herein, the terms "treatment," "treating," "treat" and the like, refer to obtaining a desired pharmacologic and/or physiologic effect. The terms are also used in the context of the administration of a "therapeutically effective amount" of an agent, e.g., a stem cell mobilizer. The effect may be prophylactic in terms of completely or partially preventing a particular outcome, disease or symptom thereof and/or may be therapeutic in terms of a partial or complete cure for a disease and/or adverse affect attributable to the disease. "Treatment," as used herein, covers any treatment of a disease or condition in a subject, particularly in a human, and includes: (a) preventing the disease or condition from occurring in a subject which may be predisposed to the disease or condition but has not yet been diagnosed as having it; (b) inhibiting the disease or condition, i.e., arresting its development; and (c) relieving the disease or condition, e.g., causing regression of the disease or condition, e.g., to completely or partially remove symptoms of the disease or condition. In particular embodiments, the term is used in the context of treating a subject with acute liver injury.

II. Stem Cell Mobilizers

The present invention relates to the treatment of subjects with acute liver injury with at least one stem cell mobilizer. Generally, stem cell mobilizers include, but are not limited to, small organic molecules, polypeptides, nucleic acids, and carbohydrates.

In the case of a polypeptide, the stem cell mobilizer may comprise a cytokine, a colony stimulating factor, a protease or a chemokine. More specifically, the cytokine can include, but is not limited to, interleukin-1 (IL-1), interleukin-3 (IL-3), interleukin-6 (IL-6), interleukin-11 (IL-11), interleukin-7 (IL-7), and interleukin-12 (IL12).

In the case of a colony stimulating factor, the stem cell mobilizer can include, but is not limited to, granulocyte colony stimulating factor (G-CSF), granulocyte-macrophage colony stimulating factor (GM-CSF), macrophage colony stimulating factor (M-CSF), stem cell factor, FLT-3 ligand or a combination thereof.

In other embodiments, the protease stem cell mobilizer can include, but is not limited to, metalloproteinase (like MMP2 or MMP9) a serine protease, (like cathepsin G, or elastase) a cysteine protease (like cathepsin K) and a dipeptidyl peptidase-1 (DDP-1 OR CD26).

In yet further embodiments, the chemokine stem cell mobilizer can include, but is not limited to, CXCL12, IL-8, Mip-1α, and Groβ.

In other embodiments, the nucleic acid stem cell mobilizer is a DNA or an RNA molecule. In more specific embodiments, the nucleic acid can be a small interfering RNA (siRNA) molecule or an antisense molecule specific for CXCL12.

In the case of a carbohydrate, the stem cell mobilizer can be a sulfated carbohydrate and can include, but is not limited to, Fucoidan and sulfated dextran. Fucoidan is a carbohydrate consisting of L-fucose, sulfate and acetate in a molar proportion of 1:1.23:0.36 and can be isolated from the Pacific brown seaweed Fucus evanescens. See Bilan et al., 337(8) CARBOHYDRATE RESEARCH 719-30 (2002). Sulfated dextrans refer to a series of polysaccharides that have variable sulfated patterns. See, e.g. Pomin et al., 15(12) GLYCOBIOLOGY 1376-1385 (2005); Melo et al., 279(2) J. BIOL. CHEM. 20824-20835 (2004); and Farias et al., 275(38) J. BIOL. CHEM. 29299-29307 (2000).

Stem cell mobilizers may further include, but are not limited to, AMD3100; stromal cell-derived factor (SDF-1); SDF-1 analogs (e.g., CTCE-0214 (Chemokine Therapeutics Corp.)); anti-SDF-1 antibodies; cyclophosphamide; stem cell factor (SCF); filgrastim; ancestim; Myeloid Progenitor Inhibitory Factor-1 (MPIF-1) (see U.S. Patent Publication No. 20080274109); and Very Late Antigen (VLA-4) antagonists (e.g., an alpha-4 integrin antagonist, such as an antibody including Natalizumab or Anti-phospho-Integrin α4 (Ser988), clone 6.33 (Upstate Cell Signaling Solutions), or a peptide (e.g., phenylacetyl-leu-asp-phe-D-prolineamide (Cytel Corp., San Diego Calif.))).

In particular embodiments, the stem cell mobilizer comprises a CXCR4 antagonist. In specific embodiments, the CXCR4 antagonist is TG-0054 (TaiGen Biotechnology Co., Ltd. (Taipei, Taiwan)). In other specific embodiments, the CXCR4 antagonist is AMD3465. In yet other embodiments, the CXCR4 antagonist is AMD3100. AMD3100 (1,1'-[1,4-phenylenebis(methylene)]bis-1,4,8,11-tetraazacyclo-tetradecane) is a symmetric bicyclam, prototype non-peptide antagonist of the CXCR4 chemokine receptor. See U.S. Pat. Nos. 6,835,731 and 6,825,351. The term "AMD" or "AMD3100" is used interchangeably with plerixafor, rINN, USAN, JM3100, and its trade name, Mozobil™. In other embodiments, the CXCR4 antagonist is NIBR1816 (Novartis, Basel, Switzerland)

The present invention also contemplates using mimetics of AMD3100. Mutational substitutions at 16 positions located in TM-III, -IV, -V, -VI, and -VII lining the main ligand-binding pocket of the CXCR4 receptor have identified three acid residues: $Asp^{171}$ (AspIV:20), $Asp^{262}$ (AspVI: 23), and $Glu^{288}$ (GluVII:06) as the main interaction points for AMD3100. Molecular modeling suggests that one cyclam ring of AMD3100 interacts with $Asp^{171}$ in TM-IV, whereas the other ring is sandwiched between the carboxylic acid groups of $Asp^{262}$ and $Glu^{288}$ from TM-VI and -VII, respectively. In one study, it was found that introduction of only a Glu at position VII:06 and the removal of a neutralizing Lys residue at position VII:02 resulted in a 1000-fold increase in affinity of AMD3100 to within 10-fold of its affinity in CXCR4. Thus, mimetics, such as for example, peptide or non-peptide antagonists with improved oral bioavailability can be designed to efficiently and selectively block the CXCR4 receptor.

III. Pharmaceutical Compositions and Administration

Accordingly, a pharmaceutical composition of the present invention may comprise an effective amount of at least one stem cell mobilizer. In a specific embodiment, plerixafor and G-CSF are co-administered to subject suffering from acute liver injury (e.g., ALF). As used herein, the term "effective" means adequate to accomplish a desired, expected, or intended result. More particularly, the terms "effective amount" and "therapeutically effective amount" are used interchangeably and refer to an amount of at least one stem cell mobilizer, perhaps in further combination with a second stem call mobilizer and/or optionally another therapeutic agent, necessary to provide the desired treatment or therapeutic effect, e.g., an amount that is effective to prevent, alleviate, treat or ameliorate symptoms of a disease or prolong the survival of the subject being treated. In particular embodiments, the pharmaceutical compositions of the present invention are administered in a therapeutically effective amount to treat a subject suffering from ALF. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

The pharmaceutical compositions of the present invention are in biologically compatible forms suitable for administration in vivo to subjects. The pharmaceutical compositions can further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the at least one stem cell mobilizer is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions of the present invention can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of at least one stem cell mobilizer together with a suitable amount of a pharmaceutically acceptable carrier so as to provide the form for proper administration to the patient. In particular embodiments that comprise the administration of two or more stem cell mobilizers, the stem cell mobilizers can be separately formulated and administered according to the present invention. The formulation should suit the mode of administration.

The pharmaceutical compositions of the present invention may be administered by any particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means. Most suitable routes are oral administration or injection. In certain embodiments, subcutaneous injection is preferred.

In general, the pharmaceutical compositions comprising at least one stem cell mobilizer disclosed herein may be used alone (i.e., two co-administered stem cell mobilizers) or in concert with other therapeutic agents at appropriate dosages defined by routine testing in order to obtain optimal efficacy while minimizing any potential toxicity. The dosage regimen utilizing a pharmaceutical composition of the present invention may be selected in accordance with a variety of factors including type, species, age, weight, sex, medical condition of the patient; the severity of the condition to be treated; the route of administration; the renal and hepatic function of the patient; and the particular pharmaceutical composition employed. A physician of ordinary skill can readily determine and prescribe the effective amount of the pharmaceutical composition (and potentially other agents including therapeutic agents) required to prevent, counter, or arrest the progress of the condition.

Optimal precision in achieving concentrations of the therapeutic regimen (e.g., pharmaceutical compositions comprising at least one stem cell mobilizer in combination with another therapeutic agent) within the range that yields maximum efficacy with minimal toxicity may require a regimen based on the kinetics of the pharmaceutical composition's availability to one or more target sites. Distribution, equilibrium, and elimination of a pharmaceutical composition may be considered when determining the optimal concentration for a treatment regimen. The dosages of a pharmaceutical composition disclosed herein may be adjusted when combined to achieve desired effects. On the other hand, dosages of the pharmaceutical compositions and various therapeutic agents may be independently optimized and combined to achieve a synergistic result wherein the pathology is reduced more than it would be if either was used alone.

In particular, toxicity and therapeutic efficacy of a pharmaceutical composition disclosed herein may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$.

Pharmaceutical compositions exhibiting large therapeutic indices are preferred except when cytotoxicity of the composition is the activity or therapeutic outcome that is desired. Although pharmaceutical compositions that exhibit toxic side effects may be used, a delivery system can target such compositions to the site of affected tissue in order to minimize potential damage to uninfected cells and, thereby, reduce side effects. Generally, the pharmaceutical compositions of the present invention may be administered in a manner that maximizes efficacy and minimizes toxicity.

Data obtained from cell culture assays and animal studies may be used in formulating a range of dosages for use in humans. The dosages of such compositions lie preferably within a range of circulating concentrations that include the $ED_{50}$ with little or no toxicity. The dosage may vary within this range depending upon the dosage form employed and the route of administration utilized. For any composition used in the methods of the present invention, the therapeutically effective dose may be estimated initially from cell culture assays. A dose may be formulated in animal models to achieve a circulating plasma concentration range that includes the $IC_{50}$ (the concentration of the test composition that achieves a half-maximal inhibition of symptoms) as determined in cell culture. Such information may be used to accurately determine useful doses in humans. Levels in plasma may be measured, for example, by high performance liquid chromatography.

Moreover, the dosage administration of the compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, which is entirely expressly incorporated herein by reference.

More specifically, the pharmaceutical compositions may be administered in a single daily dose, or the total daily dosage may be administered in divided doses of two, three, or four times daily. In the case of oral administration, the daily dosage of the compositions may be varied over a wide range from about 0.1 ng to about 1,000 mg per patient, per day. The range may more particularly be from about 0.001 ng/kg to 10 mg/kg of body weight per day, about 0.1-100 µg, about 1.0-50 µg or about 1.0-20 mg per day for adults (at about 60 kg).

The daily dosage of the pharmaceutical compositions may be varied over a wide range from about 0.1 ng to about 1000 mg per adult human per day. For oral administration, the compositions may be provided in the form of tablets containing from about 0.1 ng to about 1000 mg of the composition or 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the composition for the symptomatic adjustment of the dosage to the patient to be treated. An effective amount of the pharmaceutical composition is ordinarily supplied at a dosage level of from about 0.1 ng/kg to about 20 mg/kg of body weight per day. In one embodiment, the range is from about 0.2 ng/kg to about 10 mg/kg of body weight per day. In another embodiment, the range is from about 0.5 ng/kg to about 10 mg/kg of body weight per day. The pharmaceutical compositions may be administered on a regimen of about 1 to about 10 times per day.

In the case of injections, it is usually convenient to give by an intravenous route in an amount of about 0.0001 μg-30 mg, about 0.01 μg-20 mg or about 0.01-10 mg per day to adults (at about 60 kg). In the case of other animals, the dose calculated for 60 kg may be administered as well. In a specific embodiment, a plerixafor dose may comprise about 2 mg/kg, and may be administered once a day for about three days. A G-CSF dose may comprise about 300 μg/kg, and can be administered once a day for about three days.

Doses of a pharmaceutical composition of the present invention can optionally include 0.0001 μg to 1,000 mg/kg/administration, or 0.001 μg to 100.0 mg/kg/administration, from 0.01 μg to 10 mg/kg/administration, from 0.1 μg to 10 mg/kg/administration, including, but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 μg/ml serum concentration per single or multiple administration or any range, value or fraction thereof.

As a non-limiting example, treatment of subjects can be provided as a one-time or periodic dosage of a composition of the present invention 0.1 ng to 100 mg/kg such as 0.0001, 0.001, 0.01, 0.1 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Specifically, the pharmaceutical compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

The pharmaceutical compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the pharmaceutical compositions of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the pharmaceutical compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the pharmaceutical compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

The pharmaceutical compositions of the present invention (e.g., at least one stem cell mobilizer such as plerixafor (or NIBR1816) and G-CSF) can be administered simultaneously or sequentially by the same or different routes of administration. The pharmaceutical compositions may further be combined with one or more additional therapeutic agents. The determination of the identity and amount of the pharmaceutical compositions for use in the methods of the present invention can be readily made by ordinarily skilled medical practitioners using standard techniques known in the art. In specific embodiments, an effective amount of a first stem cell mobilizer of the present invention can be administered in combination with an effective amount of a second stem cell mobilizer. In other specific embodiments, a first stem cell mobilizer and a second stem cell mobilizer can be administered in combination with an effective amount of another therapeutic agent.

In various embodiments, the at least one stem cell mobilizer of the present invention (and optionally another stem cell mobilizer and/or another therapeutic agent) may be administered at about the same time, less than 1 minute apart, less than 2 minutes apart, less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In particular embodiments, two or more therapies are administered within the same patient visit.

In certain embodiments, the at least one stem cell mobilizer of the present invention (and optionally another stem cell mobilizer and/or another therapeutic agent) are cyclically administered. Cycling therapy involves the administration of a first therapy (e.g., first stem cell mobilizer) for a period of time, followed by the administration of a second therapy (e.g., a second stem cell mobilizer) for a period of time, optionally, followed by the administration of perhaps a third therapy (e.g., another therapeutic agent) for a period of time and so forth, and repeating this sequential administration, e.g., the cycle, in order to reduce the development of resistance to one of the therapies, to avoid or reduce the side effects of one of the therapies, and/or to improve the efficacy of the therapies. In certain embodiments, the administration of the combination therapy of the present invention may be repeated and the administrations may be separated by at least 1 day, 2 days, 3 days, 5 days, 10 days, 15 days, 30 days, 45 days, 2 months, 75 days, 3 months, or at least 6 months.

Thus, in one aspect, a first stem cell mobilizer is administered in combination with a second stem cell mobilizer. In particular embodiments, the first stem cell mobilizer (e.g., plerixafor or NIBR1816) and second stem cell mobilizer (e.g., G-CSF) are administered separately over a period of time following injury (e.g., ALF). For example, the treatment regimen for a patient suffering from ALF may comprise the following: plerixafor (2 mg/kg) and G-CSF (300 µg/kg) at Day 0, 1, 2, and 3 (subcutaneous injection). In other embodiments, the dosage regimen for a patient may comprise NIBR1816 (30 mg/kg) and G-CSF (300 µg/kg).

Alternatively, plerixafor can be administered in a dose of about 10 µg to about 10 mg per kg of body weight, about 100 µg to about 5 mg per kg of body weight, about 200 µg to about 3 mg per kg of body weight, about 300 µg to about 2 mg per kg of body weight, or any range or value of the foregoing. In one embodiment, the dose of plerixafor can be about 1 mg to about 4 mg/kg. In a specific embodiment, plerixafor can be administered at a dose of about 2 mg/kg of body weight.

Such doses can be administered within about 1 hour to about 96 hours following injury (e.g., acute liver injury, acute liver failure, ischemic injury, etc.), within about 1 hour to about 72 hours, within about 1 to about 48 hours, within about 1 to about 24 hours, and within about 2 hours to about 12 hours following injury. In the cases of transplant, plerixafor can be administered several days to several hours prior to surgery.

Other CXCR4 antagonists like NIBR1816 can be administered in a dose of about 1 mg to about 60 mg per kg of body weight, about 10 mg to about 50 mg per kg of body weight, about 20 mg to about 40 mg per kg of body weight, about 25 µg to about 45 mg per kg of body weight, or any range or value of the foregoing. In one embodiment, the dose of NIBR1816 can be about 25 mg to about 35 mg/kg. In a specific embodiment, NIBR1816 can be administered at a dose of about 30 mg/kg of body weight.

A CXCR4 antagonist like TG-0054 can be administered in a dose of about 0.1 mg to about 10 mg per kg of body weight, about 0.5 mg to about 8 mg per kg of body weight, about 1 mg to about 6 mg per kg of body weight, about 1.5 mg to about 5 mg per kg of body weight, or any range or value of the foregoing. In one embodiment, the dose of TG-0054 can be about 2 mg to about 5 mg/kg. In a specific embodiment, TG-0054 can be administered at a dose of about 4 mg/kg of body weight.

Such doses of CXCR4 antagonists can be administered within about 1 hour to about 96 hours following injury (e.g., acute liver injury, acute liver failure, ischemic injury, etc.), within about 1 hour to about 72 hours, within about 1 to about 48 hours, within about 1 to about 24 hours, and within about 2 hours to about 12 hours following injury. In the cases of transplant, a stem cell mobilizer (e.g., a CXCR4 antagonist) can be administered several days to several hours prior to surgery.

G-CSF can be administered in a dose of about 1 µg to about 3 mg per kg of body weight, about 5 µg to about 2 mg per kg, about 10 µg to about 1 mg per kg, about 50 µg to about 900 µg per kg, and about 100 µg to about 500 µg per kg, or any range or value of the foregoing. In certain embodiments, the dose of G-CSF can be about 200 µg to about 400 µg per kg. In a specific embodiment, G-CSF can be administered at a dose of about 300 µg/kg of body weight.

Such doses can be administered within about 1 hour to about 96 hours following injury (e.g., acute liver injury, acute liver failure, ischemic injury, etc.), within about 1 hour to about 72 hours, within about 1 to about 48 hours, within about 1 to about 24 hours, and within about 2 hours to about 12 hours following injury. In the cases of transplant, G-CSF can be administered several days to several hours prior to surgery.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Rodent models of Acute Liver Failure. Female Lewis rats or C57BL/6 mice were administered various doses of carbon tetrachloride ($CCl_4$) (Sigma) via intraperitoneal injection to determine the sublethal dose that would best recapitulate ALF in humans. $CCl_4$, was dissolved in mineral oil to a final of concentration of fifty percent (50%) for mice and twenty five percent (25%) for rats, and was administered by single intraperitoneal injection at doses ranging from 2 ml/kg to 4.5 ml/kg under inhaled isoflurane anesthesia. To account for the inherent variability in survival and severity of injury after $CCl_4$, injection, each treatment group was comprised of eight to ten animals. For characterization of hepatic injury in response to $CCl_4$ injection, animals were sacrificed daily for measurement of serum transaminases (aspartate transaminase (AST) and alanine transaminase (ALT)), and for histopathologic analysis of liver injury. All experimental regimens were repeated for survival analyses and animals were observed for up to 16 days.

All animals were housed in an approved microisolation facility with free access to food and water in a light-cycled room. All experimental protocols were approved by the Johns Hopkins University Institutional Animal Care and Use Committee.

Mobilization of HSCs. For HSC mobilization, plerixafor and G-CSF were administered by subcutaneous injection at weight-based doses consistent with those that have proven effective in human clinical trials or as has been used previously by the present inventors (plerixafor, 2 mg/kg/dose; G-CSF 300 µg/kg/dose). Plerixafor and G-CSF were administered 12-hours following $CCl_4$ injection, in treatment groups comprised of eight to ten animals. Control treatment groups were administered an injection with an equivalent volume of saline.

Flow Cytometric Analysis of Peripheral Blood. Following HSC mobilization, animals were sacrificed at either one or six hours post treatment and blood was collected. Leukocyte suspensions ($1 \times 10^6$) of peripheral blood were analyzed for CD34, Thy-1 and c-Kit expression. Nonspecific antibody binding was blocked with mouse and donkey serum (Sigma) for 30 minutes. The cells were incubated with Alexa Fluor 647 conjugated mouse anti-rat CD34 (1:10) (Santa Cruz Biotechnology), fluorescein isothiocyanate (FITC)-conjugated mouse anti-rat CD90 (Thy-1, 1:100) (BD Pharmingen), and rabbit anti-rat c-Kit (1:100) (Santa Cruz Biotechnology) for 45 minutes at 4° C., followed by phycoerythrin (PE)-conjugated donkey anti-rabbit IgG (1:200) (eBioscience) for 30 minutes at 4° C. The CD34, Thy-1 and c-Kit positive cells were counted by flow cytometry using CELL-Quest software (Becton-Dickinson).

Histology and Immunohistochemistry. Frozen sections of 5 µm cut serially were fixed with acetone at −20° C. for 10 minutes and dried for 1 hour at room temperature. The streptavidin-biotin-peroxidase method with the DAKO Kit (Carpinteria, Calif.) was used to detect CD34 antigen. After the blocking of nonspecific binding of antibody, the specimens were reacted with goat anti-CD34 (1:100) (R&D Systems, Inc) at 4° C. overnight. Subsequently, the sections were incubated with Biotin-SP-conjugated bovine anti-goat IgG (1:200) (Jackson Laboratories) at room temperature for 30 minutes. Diaminobenzidine tetrahydrochloride was used as the chromogen, and hematoxylin was used for counterstaining.

Example 1

Figures 1A, 1C:
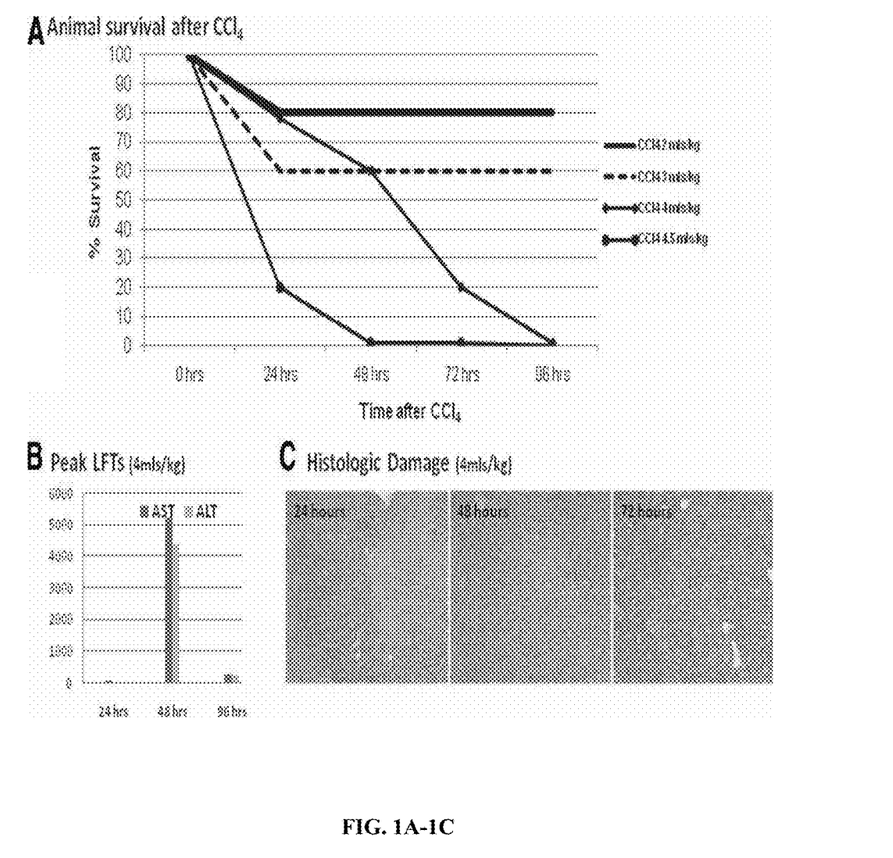
FIG. 1A is a graph showing percent survival over four days among groups (n=10) of mice administered intraperitoneal injections of $CCL_4$ at doses of 2 ml/kg (solid line), 3 ml/kg (dashed line), 4 ml/kg (diamond markers), or 4.5 ml/kg (circle markers).
FIG. 1C shows hematoxalin and eosin staining of mouse livers at 24 hrs, 48 hrs, and 72 hrs after intraperitoneal injection of $CCl_4$.

Carbon Tetrachloride ($CCL_4$) Administration Recapitulates Acute Liver Failure (ALF) in Rodents Animals that were treated with increasing amounts of $CCL_4$ showed a dose-dependent decrement in survival (FIG. 1A). Groups of ten animals that were treated with 2 ml/kg routinely showed one or two mortalities per ten within the first one to two days after treatment. The large majority of animals in this group were transiently ill but rapidly regained vigor. Animals that received 3 ml/kg showed higher mortality rates, typically 3 or 4 animals died but reliably more than half recovered spontaneously. A dose of 4 ml/kg would result in about 60% to 100% mortality among the animals over the course of three to seven days. Slight adjustments in the dose (i.e., 4.5 ml/kg) at this level would have obvious effects on mortality with all animals succumbing within 24-48 hours.

A dose of 4 ml/kg was eventually selected for the final model. Mortality with this dose was typically about 80% around five days and was preceded by a significant elevation in serum transaminases. AST and ALT levels peaked at approximately 5,000 on day one to two after injury (FIG. 1B). Histologic examination of rodent livers after injury revealed marked inflammation and necrosis which increased over the first three days (FIG. 1C). Injured livers displayed penetrating inflammatory cells and increased hepatocyte vacuolization as well as apoptotic bodies consistent with severe injury.

There was low but persistent variability between groups of animals and batches of $CCL_4$ based on baseline animal vigor at time of delivery to our institution, strength of drug, and efficacy of delivery by injection.

Example 2

Plerixafor and G-CSF Mobilize a Population of CD34+ HSCs in Rodents

Figures 2A, 2C:
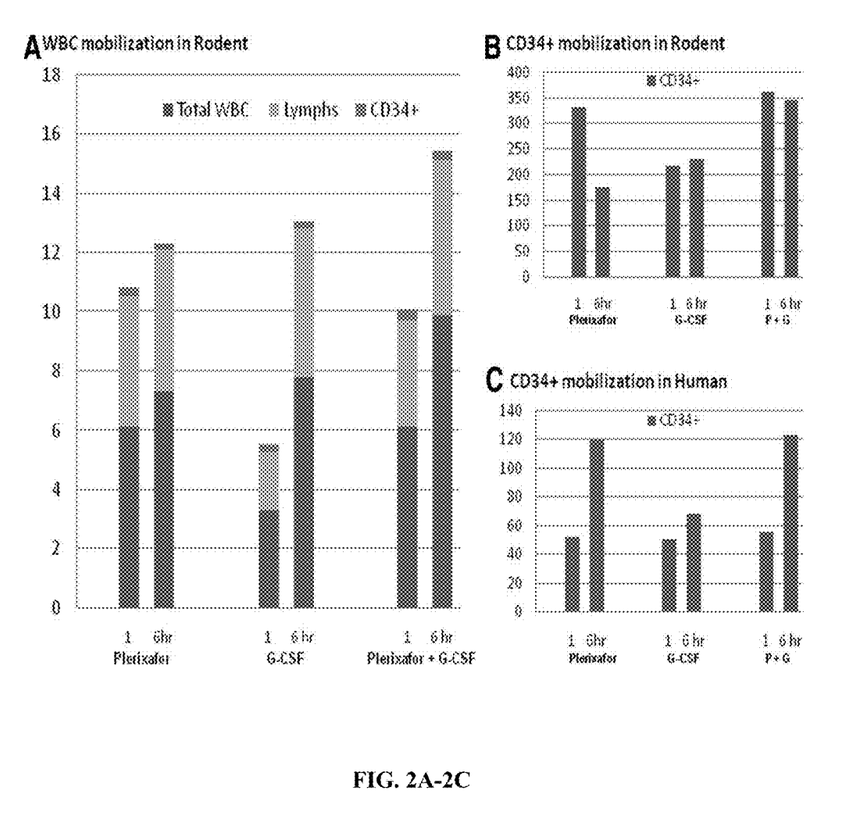
In FIG. 2A, peripheral total white blood cell (WBC) count, total lymphocytes, and $CD34^+$ cells were measured in serum by FACS analysis at 1 hr and 6 hrs after injection.
FIG. 2C shows mobilization of $CD34^+$ cells in human after administration of plerixafor and/or G-CSF. See Mozobil (plerixafor injection) Product Monograph 2009 (Genzyme Corporation, Cambridge, Mass.).

Rats that received either plerixafor or G-CSF showed an increase in their peripheral white blood cell (WBC) counts at 1 and 6 hours (FIG. 2A). Animals receiving plerixafor alone had an average total WBC of 6,100 at one hour (n=3) and 7,300 at 6 hours (n=3). Animals receiving G-CSF alone had average total WBCs of 3,300 at 1 hour (n=3) and 7,800 at 6 hours (n=3). Animals receiving both drugs had an average total WBC count of 6,000 at 1 hour (n=3) and of 9,900 at 6 hours (n=3).

The lymphocyte compartment, which is thought to contain the majority of HSCs showed similar changes (FIG. 2A). Animals receiving plerixafor had total lymphocyte counts of 4,400 and 4,800 at one and six hours respectively. Animals receiving G-CSF had total lymphocyte counts of 2,000 and 4,100 at one and six hours respectively. Animals receiving both drugs had total lymphocyte counts of 3,600 and 5,200 at one and six hours respectively.

$CD34^+$ cells were increased in all three treatment groups (FIG. 2B). Animals that received plerixafor alone had peripheral $CD34^+$ absolute counts of 333 cells/ml and 135 cells/ml at one and six hours, respectively. Animals that received G-CSF alone had absolute $CD34^+$ cell totals of 216 cells/ml and 238 cells/ml at one and six hours. Animals that received both drugs had peripheral CD34+ cells counts of 363 cells/ml and 346 cells/ml.

Though rats have a wider distribution of "normal" starting peripheral WBC counts, the mobilization results shown closely mirrors that known to occur after administration of these agents in humans whom likewise show a robust increase at 6 hours (FIG. 2C) which peaks at 9 hours. See Mozobil (plerixafor injection) Product Monograph 2009 (Genzyme Corporation, Cambridge, Mass.). Administration of both agents together resulted in the greatest increase in serum WBCs. Analysis of the mobilized population showed it to be enriched with CD34+ HSCs (FIG. 2B) with the greatest absolute CD34+ numbers in the serum of animals treated with both plerixafor and G-CSF. This response is similar to that seen in humans after administration of plerixafor and G-CSF.

Example 3

Stem Cell Mobilization Improves Survival in an Animal Model of ALF

Figure 3A:
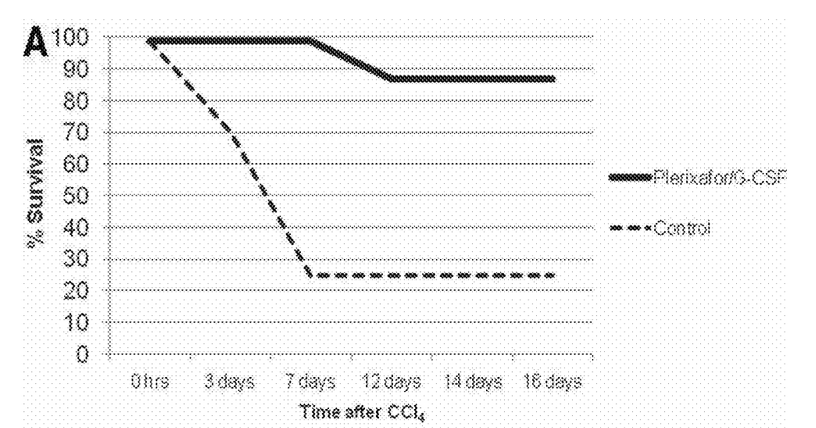
FIG. 3A shows percent survival over 16 days among groups (n=8) of mice administered intraperitoneal injections of $CCL_4$ (4 ml/kg) and treated with 2 mg/kg/d plerixafor and 300 µg/kg/d G-CSF for 3 days (solid line) or saline control (dashed line).
Figure 3B:
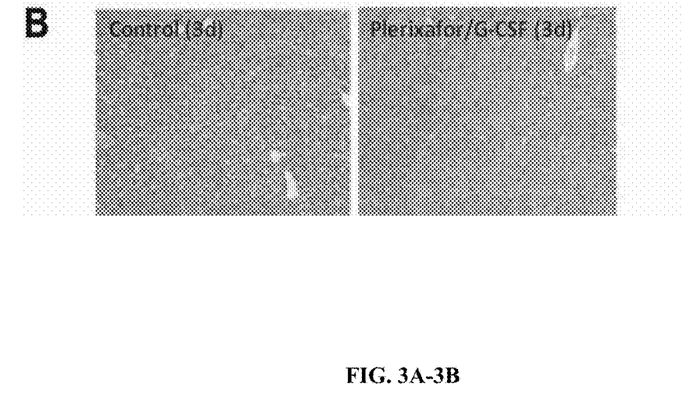
FIG. 3B shows representative hematoxalin and eosin stained sections of liver from $CCL_4$ injected mice three days after treatment with saline control, or plerixafor and G-CSF.

Rodents (n=8) that were administered intraperitoneal $CCl_4$ (4 ml/kg) displayed a high rate of mortality (75% at 6-7 days) consistent with the model. In contrast, animals (n=8) that received an identical injury (4 ml/kg) but twelve hours later initiated plerixafor (2 mg/kg/d×3d) and G-CSF (300 µg/kg/d×3d) survived at a much higher rate (13% mortality) (FIG. 3A). Examination of liver specimens from intentionally sacrificed animals from the treated and untreated groups after injury showed lesser histologic injury in the group that had received stem cell mobilization (FIG. 3B).

Example 4

Figure 4A:
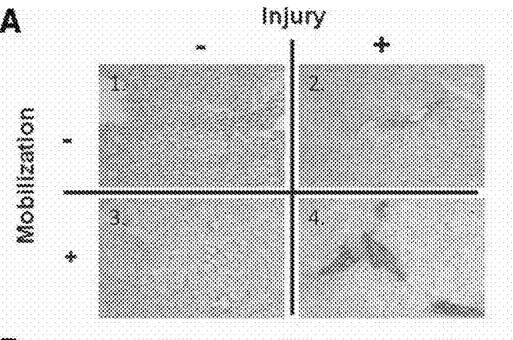
Figure 4B:
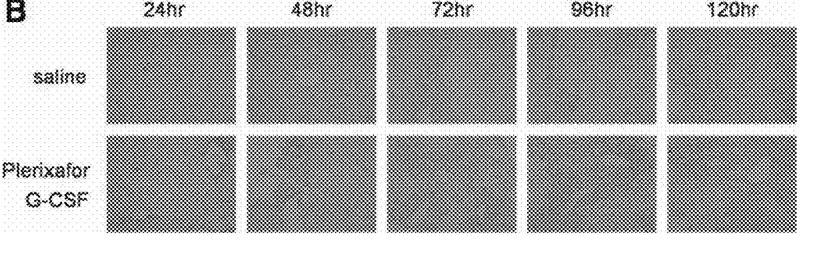
FIG. 4B shows CD34 immunostaining over the first 5 days after injury in animals that were treated with stem cell-mobilizing agents versus control.

Animals that have Undergone Stem Cell Mobilization after Liver Injury Show CD34+ HSCs Infiltrating their Livers Animals that underwent $CCL_4$ injury (or control vehicle) and stem cell mobilization (or control saline injection) were sacrificed at days 1 or 3 and underwent hepatectomy. Thin slide microscopy after staining with antibodies specific for CD34 revealed the presence of significant periportal infiltrating HSCs at 24 hours (FIG. 4A, panel 4). Conversely, animals that had undergone injury only (FIG. 4A, panel 3), or had been treated with mobilizing agents but no injury (FIG. 4A, panel 2) displayed far fewer $CD34^+$ cells in hepatectomy specimens. Animals that received neither injury nor stem cell mobilization showed no $CD34^+$ staining at 24 hours (FIG. 4A, panel 1). FIG. 4B shows increased CD34+ staining over 5 days in animals that were injured and underwent stem cell mobilization.

Example 5

Effective Mobilization of Pig Bone-Marrow Derived Stem Cells with Plerixafor

Figure 5:
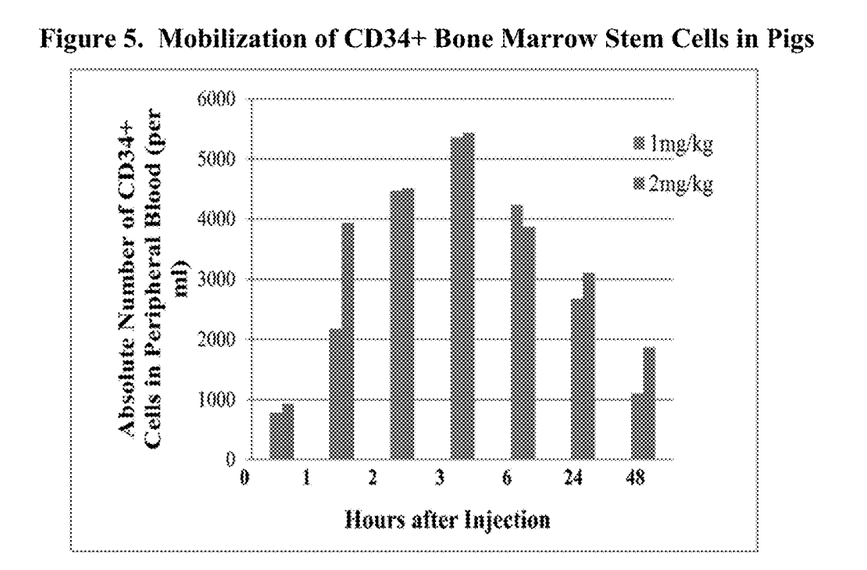
FIG. 5 shows the effective mobilization of CD34+ bone marrow stem cells in pigs.

The dosage of plerixafor used in swine transplants was based on the experiments in rats. It is possible that the effective dosage of plerixafor will differ among species. The efficacy of plerixafor was tested in non-transplanted pigs and blood cell count and flow cytometric analysis were used to measure $CD34^+$ stem cells in peripheral blood. FIG. 5 shows that the absolute number of $CD34^+$ cells in per ml blood was significantly increased in a time-dependent fashion, and reached peak levels at 3 hours after subcutaneous injection of plerixafor. Interestingly, there was no significant difference in the number of $CD34^+$ cells between two different dosages of plerixafor (1 mg/kg or 2 mg/kg) at 2, 3 and 6 hours after injection. These results indicate that effective dosage of plerixafor in pigs may be same as found in rats.

Example 6

Successful Establishment of a Pig Liver Transplant Model

Figures 6A, 6I:
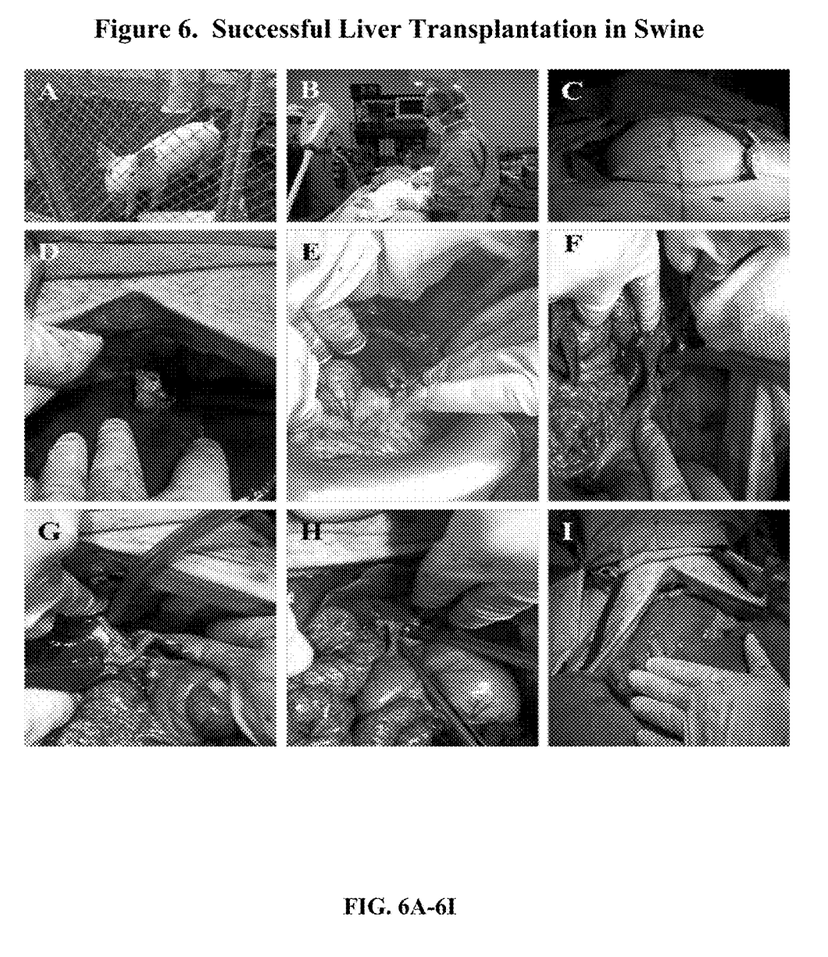

A swine pre-clinical liver transplant model was successfully established. Utilizing 20 kg miniature swine (FIG. 6A) in a large animal operating room (FIG. 6B), orthotopic liver transplantations were successfully performed in under 3 hours for both donor and recipient procedures (n=5). Utilizing a midline laparotomy in the recipient (FIG. 6C), a hepatectomy was performed after the donor organ had been procured. Transplantation consisted of a suprahepatic (FIG. 6D) and infrahepatic (FIG. 6E) vena caval anastomosis followed by reconnection of the portal vein (FIG. 6F) and graft reperfusion. The hepatic artery was sewn after an aortic conduit had been constructed utilizing donor iliac artery (FIG. 6G), and finally the bile duct anastomosis was constructed in an end-to-end fashion (FIG. 6H). The liver had a normal appearance at the end of the procedure (FIG. 6I) and the animals tolerated the relatively short operation well. Long-term function is assayed utilizing procedures known to those of ordinary skill in the art. Based on the appearance and texture of the liver after the transplant, it is expected that the pig liver transplant model will become a routine procedure. $CD34^+$ stem cells will be mobilized using the methods of the present invention in this pig liver transplant model. It is expected that stem cell mobilization using at least one stem cell mobilizer (e.g., plerixafor and G-CSF) will facilitate quicker recovery, the ability to use ever more extended criteria grafts or ever smaller living donor grafts (which would then serve as scaffolds for endogenous repopulation by mobilized host stem cells), and/or the conversion of donor graft to recipient phenotype.

I claim:

1. A method for treating a subject with acute liver injury comprising administering to the subject a therapeutically effective amount of plerixafor and granulocyte colony stimulating factor (G-CSF) to mobilize CD34+ stem cells from the bone marrow into the peripheral blood.

2. The method of claim 1, wherein plerixafor is administered in a range of about 200 μg to about 3 mg per kg of body weight.

3. The method of claim 2, wherein plerixafor is administered in a dose of about 2 mg/kg of body weight.

4. The method of claim 1, wherein G-CSF is administered in a range of about 10 μg to about 1 mg/kg of body weight.

5. The method of claim 4, wherein G-CSF is administered in a dose of about 300 μg/kg of body weight.

6. The method of claim 1, wherein the acute liver injury comprises acute liver failure.

7. The method of claim 1, wherein the acute liver injury comprises post-surgical resection.

8. A method for treating a subject with acute liver failure comprising administering to the subject a therapeutically effective amount of plerixafor and granulocyte colony stimulating factor (G-CSF) to mobilize CD34+ stem cells from the bone marrow into the peripheral blood.

9. The method of claim 8, wherein plerixafor is administered in a range of about 200 μg to about 3 mg per kg of body weight.

10. The method of claim 9, wherein plerixafor is administered in a dose of about 2 mg/kg of body weight.

11. The method of claim 8, wherein G-CSF is administered in a range of about 10 μg to about 1 mg/kg of body weight.

12. The method of claim 11, wherein G-CSF is administered in a dose of about 300 μg/kg of body weight.

* * * * *